US009899279B2

(12) United States Patent
Bernier et al.

(10) Patent No.: US 9,899,279 B2
(45) Date of Patent: Feb. 20, 2018

(54) FLAT LAMINATE, SYMMETRICAL TEST STRUCTURES AND METHOD OF USE TO GAUGE WHITE BUMP SENSITIVITY

(71) Applicant: INTERNATIONAL BUSINESS MACHINES CORPORATION, Armonk, NY (US)

(72) Inventors: William E. Bernier, Endwell, NY (US); Timothy H. Daubenspeck, Colchester, VT (US); Virendra R. Jadhav, Wappingers Falls, NY (US); Valerie A. Oberson, Quebec (CA); David L. Questad, Hopewell Junction, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 592 days.

(21) Appl. No.: 14/517,053

(22) Filed: Oct. 17, 2014

(65) Prior Publication Data
US 2015/0036716 A1 Feb. 5, 2015

Related U.S. Application Data

(62) Division of application No. 13/277,246, filed on Oct. 20, 2011, now Pat. No. 8,957,531.

(51) Int. Cl.
*H01L 23/538* (2006.01)
*H05K 1/18* (2006.01)
(Continued)

(52) U.S. Cl.
CPC .............. *H01L 22/30* (2013.01); *B05D 1/36* (2013.01); *G01N 25/16* (2013.01); *G01N 3/60* (2013.01); *G01N 19/04* (2013.01); *G01N 2203/0296* (2013.01); *G01N 2203/0298* (2013.01); *H01L 24/13* (2013.01); *H01L 2224/131* (2013.01);
(Continued)

(58) Field of Classification Search
CPC ............... H01L 22/30; H01L 2924/351; H01L 2224/131; H01L 24/13; H01L 2924/10253; H01L 2924/014; H01L 2924/00; G01N 25/16; G01N 3/60; G01N 19/04; G01N 2203/0296; G01N 2203/0298; B05D 1/36
See application file for complete search history.

(56) References Cited

U.S. PATENT DOCUMENTS 4,563,383 A 1/1986 Kuneman et al.
4,996,116 A 2/1991 Webster et al.
(Continued)

FOREIGN PATENT DOCUMENTS

CN 1507312 6/2004

*Primary Examiner* — Randy Gibson
(74) *Attorney, Agent, or Firm* — Steven J. Meyers; Andrew M. Calderon; Roberts Mlotkowski Safran Cole & Calderon, P.C.

(57) ABSTRACT

A symmetrical, flat laminate structure used to minimize variables in a test structure to experimentally gauge white bump sensitivity to CTE mismatch is disclosed. The test structure includes a flat laminate structure. The method of using the test structure includes isolating a cause of a multivariable chip join problem that is adversely impacted by warpage and quantifying a contribution of the warpage, itself, in a formation of the multivariable chip join problem.

10 Claims, 4 Drawing Sheets

(51) Int. Cl.
  *B05D 1/36* (2006.01)
  *G01N 25/16* (2006.01)
  *H01L 21/66* (2006.01)
  *H01L 23/00* (2006.01)
  *G01N 3/60* (2006.01)
  *G01N 19/04* (2006.01)

(52) U.S. Cl.
  CPC .............. *H01L 2924/10253* (2013.01); *H01L 2924/351* (2013.01)

(56) References Cited

U.S. PATENT DOCUMENTS

| | | | |
|---|---|---|---|
| 5,100,740 A | 3/1992 | Neugebauer et al. | |
| 5,483,421 A | 1/1996 | Gedney et al. | |
| 5,486,421 A | 1/1996 | Kobayashi | |
| 5,874,152 A | 2/1999 | Middleman | |
| 6,692,588 B1 | 2/2004 | Uzoh et al. | |
| 6,841,738 B2 | 1/2005 | Michiwaki et al. | |
| 6,862,189 B2 * | 3/2005 | Higuchi | H01L 25/50 257/686 |
| 6,876,088 B2 * | 4/2005 | Harvey | H01L 25/0657 257/686 |
| 6,905,912 B2 * | 6/2005 | Maeda | H01L 24/81 257/E21.705 |
| 7,154,189 B2 * | 12/2006 | Maeda | H01L 24/81 257/687 |
| 7,161,238 B2 | 1/2007 | Hsieh et al. | |
| 7,170,165 B2 | 1/2007 | Berto et al. | |
| 7,240,429 B2 * | 7/2007 | Shiraishi | H01L 21/4857 174/260 |
| 7,339,794 B1 | 3/2008 | Wang et al. | |
| 7,343,671 B2 * | 3/2008 | Hetherton | H01C 1/1406 156/228 |
| 7,382,627 B2 * | 6/2008 | Borland | H01C 7/005 361/738 |
| 7,477,522 B2 | 1/2009 | Hazelzet | |
| 7,614,145 B2 * | 11/2009 | Wakizaka | H05K 3/389 174/259 |
| RE42,252 E | 3/2011 | Clayton et al. | |
| 7,958,477 B2 | 6/2011 | Daubenspeck et al. | |
| 8,094,459 B2 * | 1/2012 | Salama | H01L 23/49894 174/256 |
| 8,957,531 B2 * | 2/2015 | Bernier | H01L 22/30 257/666 |
| 9,105,535 B2 * | 8/2015 | Blackshear | H01L 23/145 |
| 2003/0207492 A1 * | 11/2003 | Maeda | H01L 24/81 438/107 |
| 2004/0090304 A1 * | 5/2004 | Hetherton | H01C 1/1406 338/22 R |
| 2004/0118602 A1 * | 6/2004 | Lee | H05K 1/162 174/260 |
| 2004/0140528 A1 * | 7/2004 | Kim | H01F 21/12 257/537 |
| 2004/0237295 A1 * | 12/2004 | Wakizaka | H05K 3/389 29/830 |
| 2005/0068748 A1 * | 3/2005 | Ogawa | H01L 23/3121 361/748 |
| 2005/0121761 A1 * | 6/2005 | Maeda | H01L 24/81 257/678 |
| 2005/0153059 A1 * | 7/2005 | Wakizaka | C23C 18/2006 427/96.1 |
| 2006/0132277 A1 * | 6/2006 | Hetherton | H01C 1/1406 336/232 |
| 2009/0114429 A1 * | 5/2009 | Sri-Jayantha | H01L 23/49833 174/255 |
| 2010/0218364 A1 * | 9/2010 | Sri-Jayantha | H01L 23/49833 29/593 |
| 2011/0018145 A1 | 1/2011 | Salama et al. | |
| 2011/0138617 A1 | 6/2011 | Clayton et al. | |
| 2012/0111610 A1 * | 5/2012 | Kim | H01L 23/3735 174/252 |

* cited by examiner

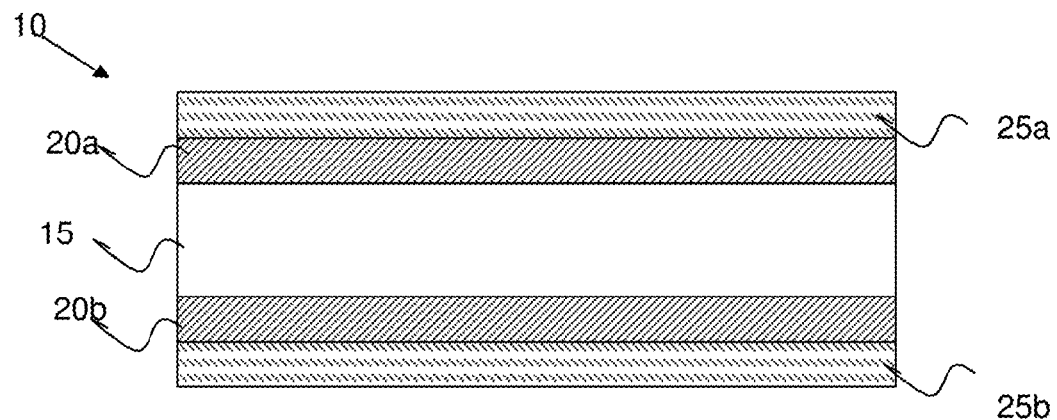
FIG. 1
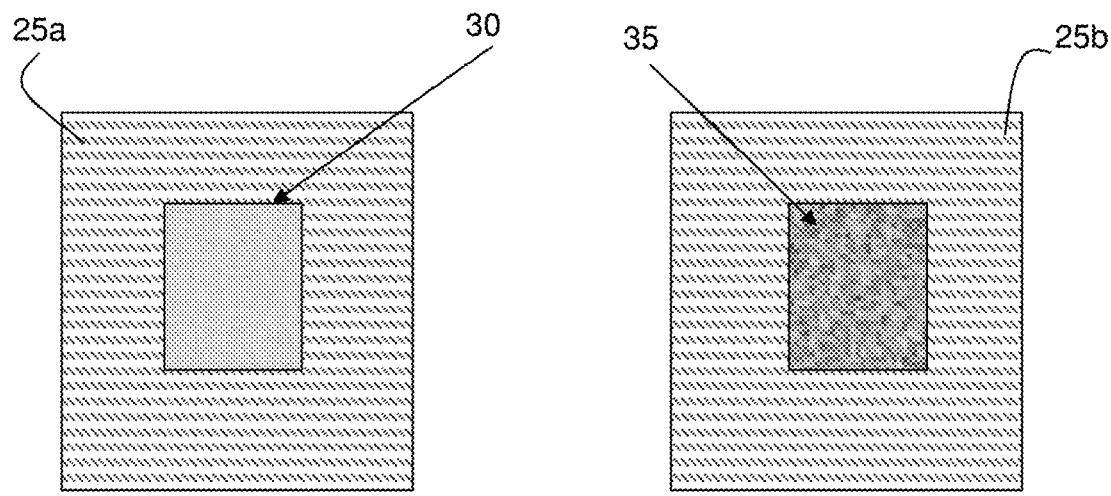
FIG. 2a
FIG. 2b

FLAT LAMINATE, SYMMETRICAL TEST STRUCTURES AND METHOD OF USE TO GAUGE WHITE BUMP SENSITIVITY

FIELD OF THE INVENTION

The invention relates to semiconductor structures and, more particularly, to a symmetrical, flat laminate structure used to minimize variables in a test structure to experimentally gauge white bump sensitivity to coefficient of thermal expansion (CTE) mismatch.

BACKGROUND

In conventional chip bonding, ceramic carriers, typically alumina, have been used as the substrate. However, the need for high-density interconnects in cost-effective chip packaging has been a motivation for using organic laminates. In contrast to ceramic substrates, organic laminates have better electrical performance at lower cost. However, when organic laminates are used for the chip assembly, incoming laminate warpage may lead to cracking or delamination of layers on the chip during the chip assembly process. Also, the warpage often results in oddly shaped solder bumps, which causes additional stress on the chip package and, possible failure of the BEOL structures such as, for example, cracking or delamination of layers, also known as white bumps. It is known incoming laminate warpage occurs due to the asymmetry of the laminates.

During the chip assembly process, the Si chip and the organic laminates also experience a temperature cycle from room temperature to the melting temperature of solder materials back to room temperature during cool down. The coefficient of thermal expansion (CTE) mismatch between a Si chip and an organic laminate creates thermally-induced stress/strain in the flip-chip structure during the chip assembly process. The thermally-induced stress/strain in the flip-chip structure also often results in a failure of the BEOL structure. This failure is becoming more common because of the fragility of low-k dielectric layers and the use of lead-free solders.

More specifically, due to the thermal expansion mismatch between organic laminates (approximately $17 \times 10^{-6}/°$ C.) and silicon chips (approximately $2.6 \times 10^{-6}/°$ C.), there are stresses produced during cool-down of the modules from the chip join temperature. In a die with fragile low-k dielectric materials in the BEOL, coupled with lead-free bump metallurgies which are stiffer than leaded bumps, the result is ultra-low dielectric constant (ULK) cracking on cool-down, i.e., "white bumps" observed by CSAM (Scanning Acoustic Microscopy in C mode).

"White bumps"/ULK cracking is a very serious problem which needs to be resolved in order to successfully implement lead-free bump technology on organic packages for 32 nm silicon technology nodes and beyond. However, when the white bump occurs in a chip, it is not clear if it is contributed by warpage or by CTE mismatch, or some other factors. Such determination would be an important factor in laminate design.

Accordingly, there exists a need in the art to overcome the deficiencies and limitations described hereinabove.

BRIEF SUMMARY

In an aspect of the invention, a test structure comprises a core material. The structure further comprises a first layer of first material formed on a first side of the core material and a second layer of the first material formed on an opposing side of the core material. The structure further comprises a layer of a second material formed on the first layer and another layer of the second material formed on the second layer.

In an aspect of the invention, a test structure comprises a core structure of insulator material. The structure further comprises a first conductive layer formed on a top side of the core structure, and a second copper layer formed on a bottom side of the core structure. The structure further comprises a first insulating dielectric layer formed on the first conductive layer, and a second insulating dielectric layer formed on the second conductive layer. The first conductive layer and the second conductive layer are of a same material and are balanced. The first insulating dielectric layer and the second insulating dielectric layer are of a same material and are balanced. The first conductive layer and the first insulating dielectric layer is in symmetry to the second copper layer and the second insulating dielectric layer.

In an aspect of the invention, a method comprises determining a cause of white bump formation on a relatively flat laminate structure, independent of incoming warpage.

BRIEF DESCRIPTION OF THE SEVERAL VIEWS OF THE DRAWINGS

The present invention is described in the detailed description which follows, in reference to the noted plurality of drawings by way of non-limiting examples of exemplary embodiments of the present invention.

FIG. 1 shows a laminate structure in accordance with aspects of the present invention;

FIG. 2a shows a top side of the laminate structure of FIG. 1;

FIG. 2b shows a bottom side of the laminate structure of FIG. 1;

DETAILED DESCRIPTION

Figure 3:
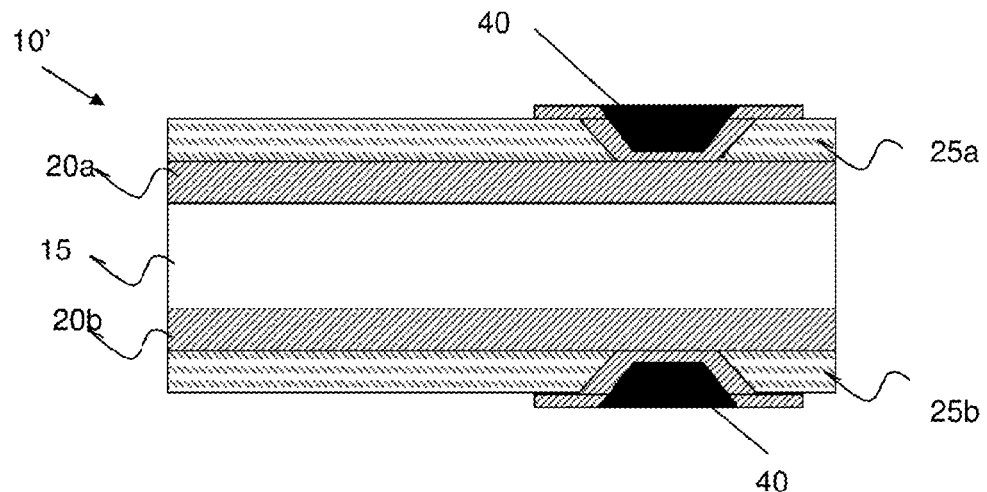
FIG. 3 shows a laminate structure in accordance with aspects of the present invention.

The invention relates to semiconductor structures and, more particularly, to symmetrical, flat laminate structures and methods of use to experimentally gauge white bump sensitivity to CTE mismatch. In embodiments, the symmetrical, flat laminate structures eliminate variables associated with asymmetrical laminate structures used in conventional solder chip bonding processes. For example, the flat, symmetrical laminate test structures of the present invention minimize incoming warpage and thermal load variables known to exist with asymmetrical laminate structures, thereby eliminating or minimizing known variables associated with white bumps or other chip join problems. In this way, advantageously, the present invention provides a method to gauge white bump sensitivity to CTE mismatch or other join problems, without any significant contributing effects associated with incoming laminate warpage.

More specifically, in one illustrative non-limiting example, white bumps are known to be caused by incoming laminate warpage and CTE mismatch between the organic substrate (laminate) and the silicon chip during chip bonding processes. As should be known to those of skill in the art, organic chip carriers (laminates) are known to have high warpage in the chip site (e.g., 30 µm range) as well as high CTE, compared to silicon. The high warpage is a result of asymmetry in the laminates, i.e., different lamination forming process, as well as different circuit designs, e.g., interconnects, wiring layers, designs, patterns, etc. placed on opposing sides of the laminates. Both the CTE mismatch and the warpage of the laminate are factors that contribute to white bump occurrence during the chip bonding process. But, prior to the present invention, it was not possible to separate the two effects (i.e., warpage and CTE mismatch) in order to attribute how each of these factors contribute to white bump formation, e.g., what is the dominating factor contributing to white bumps. Accordingly, it was not possible to design laminate structures, prior to package development.

The present invention solves this problem by providing a flat, symmetrical substrate designed to eliminate incoming laminate warpage associated with conventional asymmetrical laminate structures. For example, by implementing the present invention, it is now possible to understand a variety of issues including white bumps, underfill delamination, chip join, thermal interface performance, etc., on the chip bonding process, independent of at least one variable, e.g., warpage, which may contribute to the white bump phenomena. This, in turn, allows the focus to be on other variables which contribute to the white bump phenomena, e.g., CTE mismatch. The present invention also provides a faster and cheaper way to perform white bump evaluations, while also making it an attractive alternative to packaging development for mechanical evaluations, i.e., flush out various assembly parameters early on in package development programs.

FIG. 1 shows a laminate structure in accordance with aspects of the present invention. In embodiments, the laminate structure is a flat, symmetrical laminate 10, which comprises a core 15. The core 15 can include, for example, a glass epoxy or other insulator material. In embodiments, the core 15 can be, for example, an organic dielectric material. The core 15 can be about 0.8 mm; although other dimensions are also contemplated by the present invention.

Still referring to FIG. 1, a first layer 20a is formed on a top side of the core 15, and a second layer 20b is formed on the opposing side of the core 15. The layers 20a and 20b are formed of the same material and same thickness to ensure that the flat, symmetrical laminate 10 remains symmetrical and balanced (within certain deviations discussed herein). In embodiments, the layers 20a and 20b are copper layers formed to a thickness of about 0.015 mm+/−0.007 mm; although other conductive materials and dimensions are contemplated by the present invention. A top layer 25a is formed on the layer 20a and a bottom layer 25b is formed on the layer 20b. Like the layers 20a and 20b, the layers 25a and 25b are formed of the same material and same thickness (within certain deviations discussed herein) to ensure that the flat, symmetrical laminate 10 remains symmetrical and balanced. In embodiments, the layers 25a and 25b are front and back solder resist materials, e.g., organic dielectric material, formed to a thickness of about 0.015 mm+/−0.007 mm; although other dimensions and materials are also contemplated by the present invention. The warpage of the flat, symmetrical laminate structure 10 of the present invention is about 7 µm, by cross-section, compared to about a 25 µm for a conventional asymmetrical laminate structure.

Although not shown in FIG. 1, it should be understood by those of skill in the art that structures can be present in any of the layers 20a, 20b, 25a, and 25b. For example, the layers 20a and 20b can include wiring patterns, etc.; whereas, the layers 25a and 25b can include solder bump connections, for example. In any scenario, the present invention also contemplates that each of the corresponding layers are symmetrical, in order to reduce incoming warpage. That is, the top layers 20a and 25a of the flat, symmetrical laminate 10 are symmetrical to the bottom layers 20b and 25b of the flat, symmetrical laminate 10. However, it should be understood that there may be some slight variations between the top layers and the bottom layers, as described with respect to FIGS. 2a and 2b. These slight variations, unlike conventional organic laminate structures, will still result in minimal incoming warpage.

FIG. 2a shows a top side of the flat, symmetrical laminate structure 10 of FIG. 1; whereas, FIG. 2b shows a bottom side of the flat, symmetrical laminate structure 10 of FIG. 1. In embodiments, the top side 25a and the bottom side 25b can include the same structures or structures of the same dimensions; however, in embodiments, the top side 25a can include a lead free pre-solder region 30; whereas, the bottom side 25b can include a treated solder pads 35. In embodiments, the treated solder pads 35 can be, for example, CuOSP treated C4 pads. In embodiments, the shapes of region 30 and solder pads 35 can be identical or substantially identical on both the top side 25a and the bottom side 25b. Also, as discussed above, the region 30 and solder pads 35 can be identical structures.

FIG. 3 shows a laminate structure in accordance with aspects of the present invention. In this embodiment, the flat, symmetrical laminate structure 10' of FIG. 3 includes an identically (substantially identically) positioned, and dimensioned loading (solder landing) site 40 on each side of the structure 10'. In embodiments, the identical loading site 40 is a copper (Cu) loading site, e.g., C4 pattern for chip join. It should be understood by those of skill in the art that the flat, symmetrical laminate structure 10' of the present invention can include more than one loading site on each side of the structure.

Figure 4:
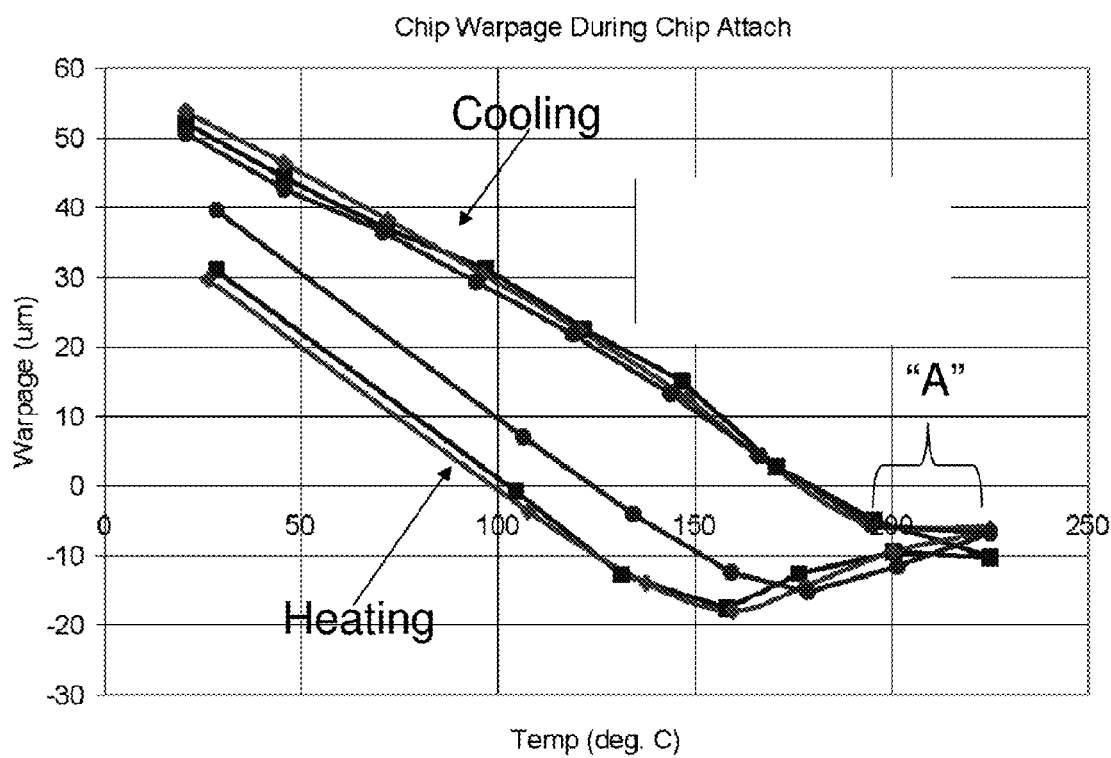
FIG. 4 shows a graph of warpage vs. temperature of a structure in accordance with aspects of the present invention.

FIG. 4 shows a graph of warpage vs. temperature of a structure of a chip joined to a substrate in accordance with aspects of the present invention. Importantly, this graph shows that the structure of the present invention is relatively flat, e.g., about 7 µm, prior to chip joining, as shown near the region of arrow "A". Also, this graph shows that the structure of the present invention remains relatively flat, e.g., about 7 µm, after a heating and cooling cycle. As in any conventional asymmetrical laminate structure, during the chip bonding process, e.g., during the actual heating and cooling, the structure will experience some warpage.

Figure 5B:
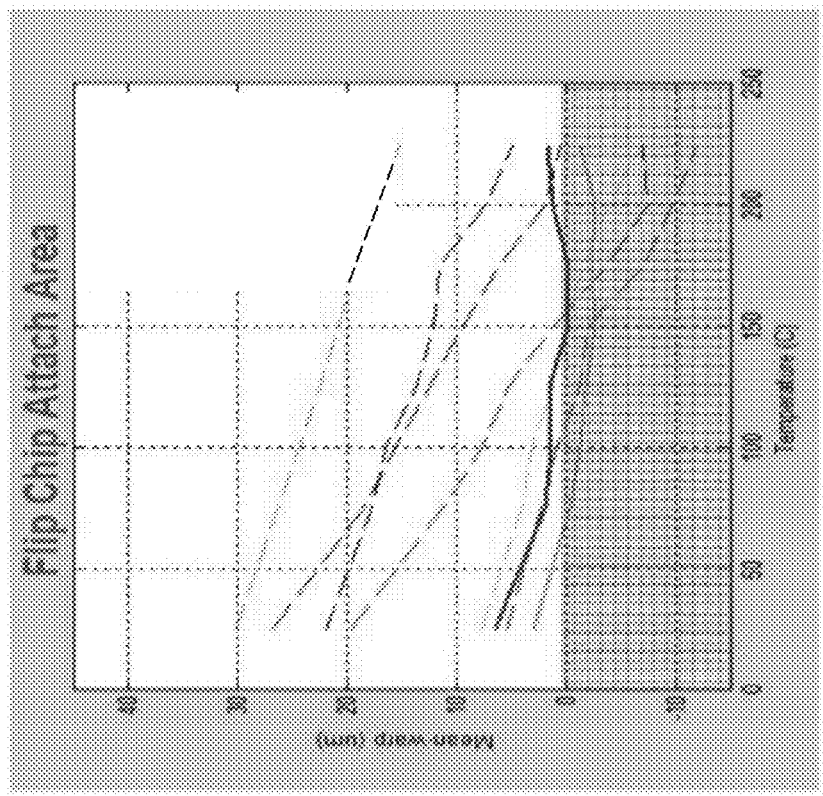
FIG. 5b shows a graph of warpage vs. temperature of a flip chip attachment area of a conventional laminate structure.
Figure 5A:
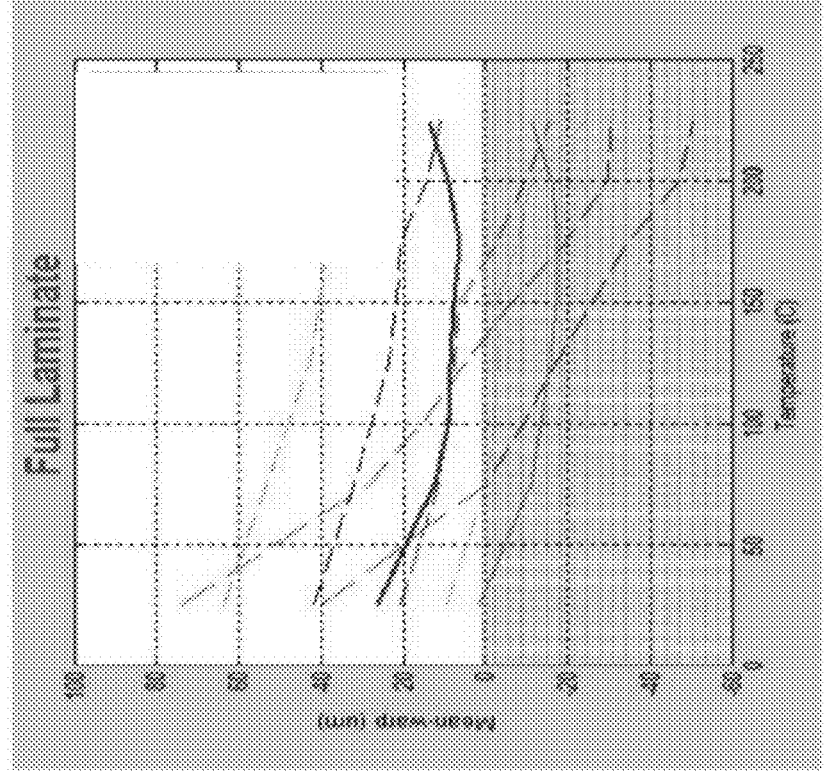
FIG. 5a shows a graph of warpage vs. temperature of a conventional laminate structure.

In comparison to FIG. 4, FIGS. 5a and 5b show different conventional organic asymmetrical laminates, each of which includes a significant incoming mean warpage. More specifically, FIG. 5a shows a graph of warpage vs. temperature of a full laminate structure with no chip attached, with the x-axis representing temperature (° C.) and the y-axis representing mean warpage in µm. FIG. 5b shows a graph of warpage vs. temperature of a flip chip attachment area, with the x-axis representing temperature (° C.) and the y-axis representing mean warpage in µm. As shown in both FIGS. 5a and 5b, the conventional organic asymmetrical laminates show a significant amount of warpage through all temperature ranges. For example, FIGS. 5a and 5b shows that some of the conventional organic asymmetrical laminates have a concave shape (in the non-shaded region above "0"), while some of the conventional organic asymmetrical laminates have a convex shape (in the shaded region below "0").

In accordance with aspects of the present invention, by using the relatively flat structures of the present invention, it is now possible to establish a technique to gauge white bump sensitivity faster than processes of record. This is due to the independent assessment of CTE, separate from white bump formation due to warpage issues. For example, it is possible to vary CTE in the laminate structure, to measure white bump sensitivity, independent of the warpage of the laminate structure. Also, it is possible to use the structures of the present invention with different back end of the line (BEOL) stackups for evaluation of white bumps, again independent of warpage issues. In this way, it is possible to use the results of experiments to optimize laminate core material in advance of program qualification build, and enables quick turnaround time (TAT) of white bump evaluation.

Table 1, below, provides a sample experiment implementing structures in accordance with the present invention, and comparing such structures to a known asymmetrical laminate structure. More specifically, Table 1 shows a conventional laminate structure #1, and compares such structure to the laminate structures of the present invention, labeled #2, #3 and #4. As should be understood by those of skill in the art, with the warpage component removed from laminates #2, #3 and #4, through the use of the flat laminates, it is now possible to directly associate white bump defect counts with CTE effects, as well as to have a quantitative assessment of the contribution of the warpage itself.

TABLE 1

|  | #1 | #2 | #3 | #4 |
|---|---|---|---|---|
| X-CTE (ppm/C.) | 18.9 | 20.4 | 16.4 | 15.0 |
| Y-CTE (ppm/C.) | 17.6 | 15.0 | 16.3 | 14.1 |
| Equivalent Diagonal CTE (ppm/C.) | 18.2 | 17.9 | 16.4 | 14.5 |
| WB Count = 0 | 0 | 0 | 1 | 3 |
| WB Count <5 | 0 | 0 | 6 | 6 |
| WB Count <10 | 4 | 3 | 3 | 1 |
| WB Count >10 | 6 | 7 | 0 | 0 |
| Average Flatness (um) | 25 | 7 | 7 | 7 |

The core structure for the laminate structure #2 is glass/epoxy such that a relatively high CTE is achieved, the core structure for the laminate structure #3 is glass epoxy such that a medium CTE is achieved, and the core structure for the laminate structure #4 is glass/epoxy such that a relatively low CTE is achieved. Also, laminates #1 and #2 have a higher CTE than the laminates #3 and #4. Moreover, laminate #1 has an average flatness of 25 μm, and the laminates #2, #3 and #4 of the present invention have an average flatness of 7 μm. the CTE of the laminates #1, #2, #3 and #4 can be approximations. As shown in the Table 1, a variation of equivalent diagonal CTE (ppm/° C.) from 18.2 ppm/° C. to 14.5 ppm/° C. was achieved, by implementing the present invention.

As shown in this experiment, the white bump count of greater than 10 for the conventional laminate structure #1 is six and the white bump count of greater than 10 for the laminate structure #2 is seven. These values are unacceptable. However, it is possible to discern from this table that the increased white bump count for the laminate #2 was due to the high CTE, and not warpage issues. However, it is not possible to determine the exact contributing factor of the white bump formation in laminate #1 due to the existence of both warpage and CTE mismatch. Moreover, Table 1 shows a white bump count of greater than 10 of 0 for both the laminates #3 and #4. Thus, this particular experiment shows that a lower CTE provides a reduced white bump count.

In fact, the know-how obtained by using the flat, symmetrical substrates of the present invention show that the focus for next generation chip carriers needs to be on lower CTE. That is, it has been found that the impact on of CTE reduction on white bump formation is significant, e.g., 3.5 ppm/° C. reduction is roughly 20% reduction in low-k or ultra low-k dielectric stress. Accordingly, improvement (e.g., reduction) of white bump formation with CTE reduction has been quantified.

The present invention also contemplates the possibility to determine the effects of other structures on white bump formation, independent of warpage. For example, it is possible to change the shape of the solder bump on the laminate to determine the effects of such shape on white bump formation, independent of warpage. This can be done by comparing the white bump count, with different shaped solders, on a same laminate composition, e.g., comparing white bump formation using different shaped solders on, e.g., laminate #3. In another example, it is possible to compare a relatively flat, symmetric laminate structure of the present invention and that of a conventional, asymmetrical laminate structure, both with the same CTE. By comparing these two structures, it is possible to determine the effect of warpage on white bump formation, with different shapes, patterns, structures, etc, e.g., interconnects, wiring layers, designs, and patterns. Thus, the flat, symmetrical laminate structures of the present invention can be used to study different BEOL stackup for white bump formation. Thus, it is now possible to vary laminate CTE to establish stress cliffs, and the results of the experiments can be used to optimize laminate core material in advance of program qualification build.

Figure 6:
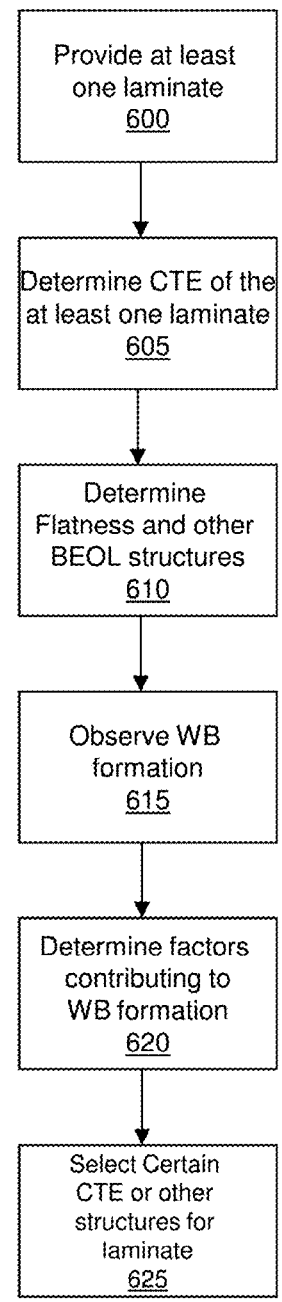
FIG. 6 is a flow diagram implementing steps in accordance with aspects of the present invention.

FIG. 6 is a flow diagram implementing steps in accordance with aspects of the present invention. It should also be noted that, in some alternative implementations, the functions noted in the block may occur out of the order noted in the figures. It will also be noted that each block of the flowchart illustration, and combinations of blocks can be implemented by special purpose hardware-based systems that perform the specified functions or acts, or combinations of special purpose hardware and computer instructions. Furthermore, the invention can take the form of a computer program product accessible from a computer-usable or computer-readable medium providing program code for use by or in connection with a computer or any instruction execution system. For the purposes of this description, a computer-usable or computer readable medium can be any apparatus that can contain, store, or communicate the program. The medium can be an electronic, magnetic, optical, electromagnetic, infrared, or semiconductor system (or apparatus or device). Examples of a computer-readable storage medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disc-read/write (CD-R/W) and DVD.

More specifically, FIG. 6 shows a method of determining a cause of white bump formation on a relatively flat laminate structure, independent of incoming warpage. More specifically, FIG. 6 shows a method of isolating a cause of a multivariable chip join problem that is adversely impacted by warpage and quantifying a contribution of the warpage, itself, in a formation of the multivariable chip join problem. These problems can be, for example, white bumps, chip-join "nonwets", and other factors that can be isolated for optimizing chip join and solder joint formation.

At step 600, the present invention provides at least one laminate structure in accordance with the present invention. At step 605, the CTE in the X, Y and equivalent diagonal direction is measured and/or determined. This measurement can be for both the flat, symmetrical laminate structure of the present invention, and/or a conventional laminate structure. At step 610, a relative flatness of the flat, symmetrical laminate structure of the present invention is measured and/or determined and/or recorded. The present invention also contemplates measuring and/or determining and/or recording other structures including, for example, solder shape, wiring, interconnects and other patterns and BEOL structures. At step 615, after a chip joining process, white bump formation is observed by, for example, CSAM, and/or other multivariable chip join problem. At step 620, a determination is made as to the effect of CTE and/or other structures, noted above in step 610, has on such problems, e.g., white bump formation (separate from incoming warpage). At step 625, a laminate with a certain CTE or structure can be selected based on the results found in step 620, which is independent of warpage.

The method as described above is used in the fabrication of integrated circuit chips. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein. Many modifications and variations will be apparent to those of ordinary skill in the art without departing from the scope and spirit of the invention. The corresponding structures, materials, acts, and equivalents of all means or step plus function elements in the claims, if applicable, are intended to include any structure, material, or act for performing the function in combination with other claimed elements as specifically claimed. Accordingly, while the invention has been described in terms of embodiments, those of skill in the art will recognize that the invention can be practiced with modifications and in the spirit and scope of the appended claims.

What is claimed:

1. A method of fabricating a flat laminate structure, the method comprising:
    forming a first layer of first material on a first side of a core material comprising insulator material;
    forming a second layer of the first material on an opposing side of the core material;
    forming a layer of a second material on the first layer; and
    forming another layer of the second material on the second layer, wherein:
    the first layer and the second layer are formed of a same thickness;
    the layer and the another layer are formed of a same thickness;
    the layer and the second layer include solder bump connections; and
    the flat laminate structure comprises the core, the first layer, the second layer, the layer and the another layer; and
    the flat laminate structure has a warpage of about 7 μm by cross section.

2. The method of claim 1, wherein the first layer and the second layer are formed from copper layers.

3. The method of claim 2, wherein the layer and the another layer are formed from a solder insulating dielectric layer.

4. The method of claim 1, wherein the core is formed from an epoxy glass.

5. The method of claim 1, further comprising forming a first structure on the layer and a second structure formed on the another layer.

6. The method of claim 5, wherein the first structure and the second structure are formed as identical solder landing structures.

7. The method of claim 1, wherein:
    the core is formed with a thickness of about 0.8 mm;
    the first layer and the second layer are formed to have a thickness of about 0.015 mm+/−0.007; and
    the layer and the another layer are formed to have a thickness of about 0.015 mm+/−0.007 mm.

8. The method of claim 1, wherein:
    the first layer and the second layer are balanced; and
    the layer and the another layer are balanced.

9. The method of claim 1, wherein the insulator material is an organic dielectric material.

10. The method of claim 1, wherein the core has a thickness of about 0.8 mm.

* * * * *